(12) United States Patent
Chen et al.

(10) Patent No.: US 11,622,975 B2
(45) Date of Patent: Apr. 11, 2023

(54) COMPOSITIONS AND METHODS FOR IMPROVED HONEY BEE HEALTH

(71) Applicant: The United States of America, as represented by the Secretary of Agriculture, Washington, DC (US)

(72) Inventors: Yanping Chen, Boyds, MD (US); Matthew C. Heerman, Beltsville, MD (US); Steven C. Cook, Capitol Heights, MD (US); Jay D. Evans, Harwood, MD (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 812 days.

(21) Appl. No.: 16/512,897

(22) Filed: Jul. 16, 2019

(65) Prior Publication Data
US 2021/0015845 A1    Jan. 21, 2021

(51) Int. Cl.
| | | |
|---|---|---|
| *A61K 31/724* | (2006.01) |
| *A01K 53/00* | (2006.01) |
| *A61P 39/02* | (2006.01) |
| *A61K 9/00* | (2006.01) |
| *A61K 31/355* | (2006.01) |
| *A61K 47/69* | (2017.01) |
| *A61P 31/04* | (2006.01) |

(52) U.S. Cl.
CPC ............ *A61K 31/724* (2013.01); *A01K 53/00* (2013.01); *A61K 9/0056* (2013.01); *A61K 31/355* (2013.01); *A61K 47/6951* (2017.08); *A61P 31/04* (2018.01); *A61P 39/02* (2018.01)

(58) Field of Classification Search
CPC .......................... A61K 31/724; A61K 47/6951
See application file for complete search history.

(56) References Cited

U.S. PATENT DOCUMENTS

| | | |
|---|---|---|
| 9,545,110 B2 | 1/2017 | Probasco et al. |
| 2019/0090507 A1 | 3/2019 | Wright et al. |

OTHER PUBLICATIONS

International Search Report dated Oct. 29, 2020 on PCT/US2020/041981.
Leblanc, Blaise W et al., "-Cyclodextrins as Carriers of Monoterpenes into the Hemolymph of the Honey Bee (*Apis mellifera*) for Integrated Pest Management" (2008) Journal of Agricultural and Food Chemistry 56:8565-8573.

*Primary Examiner* — Kevin E Weddington
(74) *Attorney, Agent, or Firm* — John D. Fado; Maria Restrepo-Hartwig

(57) ABSTRACT

Compositions comprising a mixture of at least one cyclodextrin, a carrier, and optionally one or more vitamins and/or nutrients to improve at least one health factor of a beehive is disclosed. Methods of improving beehive health and apparatuses including such compositions are also disclosed.

23 Claims, 20 Drawing Sheets

COMPOSITIONS AND METHODS FOR IMPROVED HONEY BEE HEALTH

FIELD OF THE INVENTION

The disclosed invention relates generally to novel and improved compositions for improving honey bee health and methods of making and using such compositions. More specifically, the invention relates to novel honey bee food compositions including a mixture of one or more cyclodextrins and methods of making and using such compositions to increase honey bee lifespan and improve beehive health by protecting the honey bees from various biotic and abiotic insults.

BACKGROUND OF THE INVENTION

Honey bees (Genus: *Apis*) provide critical pollination services for many agricultural crops and contribute to a significant portion of the food supply. Currently, there are approximately 2.7 million managed honey bee hives assisting the production of at least 90 commercially grown crops in the U.S. Over the past few decades, honey bee health has been a growing concern because of unusually high colony loss rates. Colony losses are likely due to the interactions of multiple factors including pesticides applied to crops where bees are foraging, pesticides to control parasites and pathogens inside beehives, mites, fungal spores (e.g., *Nosema* spores) and other pathogens (see e.g., Henry et al., 2012; Sanchez-Bayo & Goka, 2014; Frazier et al., 2015). Further studies showed that pesticides not only harm honey bees through direct toxicity but also undermine their immune system and cause other stresses (e.g., digestive stress), making them more susceptible to infectious diseases (see e.g., Alaux et al., 2010; Pettis et al., 2012; Wu et al., 2012; Vidau et al., 2011).

Managed pollinators (Genus: *Apis*) such as the European honey bee (*A. mellifera*) have become an integral part of the global agricultural landscape by providing pollination service to one-third of human food crops as well as a variety of wildlife habitats. In the U.S. alone, it is estimated that honey bees such as *A. mellifera* contribute more than 17 billion USD to the economy each year (see e.g., Calderone, 2012). Of the contributing factors to declining honey bee health, the use of pesticides might be the most harmful to honey bees and the major cause of hive collapse. Increasing applications of synthetic chemical pesticides and herbicides, while playing a critical role in defending agricultural production from damaging insects, are implicated in the declining health and populations of honey bees and other pollinators. For example, the class of synthetic pesticides referred to as neonicotinoids, such as clothianidin and imidacloprid, are some of the most widely used neuro-active insecticides for crop protection against herbivorous insects and are applied as seed treatments, foliar sprays, soil drenches, and trunk-injections. Neonicotinoids are partially water-soluble and readily taken up by plant vascular systems for distribution throughout the plant tissues, including pollen and nectar from which bees then forage. Since the mid-2000 s, there has been an increasing amount of evidence linking neonicotinoid exposure to adverse health effects on honey bees and other pollinators (see e.g., Blacquiere et al, 2012; Wood & Goulson, 2017; Woodcock et al, 2017). In addition to direct toxic effects of plant protection pesticides, honey bees are also exposed to pesticides such as pyrethroids and organophosphates used in bee colonies for controlling parasites and pests as well as pesticide residues accumulated in the hive products. Furthermore, it is thought that pesticide exposure interacts synergistically with pathogens to impair honey bee health (see e.g., (Fine, 2017; Sanches-Bayo, 2016). Numerous surveys have revealed that the pyrethroid "tau-fluvalinate" and the organophosphate "coumaphos" used as acaricides to control parasitic mites (e.g., *Varroa destructor*) are the most common contaminants present in bees and bee hive products, especially beeswax. The most popular acaricide treatment for *Varroa* mites is the formamidine compound amitraz. In a worst-case scenario, acute dosages do not immediately impair honey bee behavior and learning (see e.g., Rix & Cutler, 2017). However, there are some sublethal effects, specifically modulation of cardiac function, and lower tolerance to virus-based infection (see e.g., O'Neal, 2017).

In addition to parasitic mites and various pathogens, there are several other common beehive pests that cause an array of harm to beehives ranging from minor to catastrophic colony collapse. Small hive beetles (*Aethina tumida*) primarily cause damage to colonies in their larval stage. For example, beetle larvae burrow through the comb, feed on honey, and defecate into stored honey that leads to discoloration and fermentation of the honey making it unsuitable for sale. The larval stage of the greater wax moth (*Galleria mellonella*) and lesser wax moth (*Achroia grisella*) devastate colonies by consuming large quantities of the honeycomb. Wasps and hornets (Genus: *Vespula*) typically feed directly on honey bees. The most devastating arthropod to honey bee health is the *Varroa* mite. They replicate within the colony and feed directly on the hemolymph and fat body of honey bees causing direct damage, while also transmitting viral pathogens such as Israeli acute paralysis virus (IAPV) and Deformed wing virus (DWV).

While there are registered chemical treatments for controlling mite and beetle parasites in honey bee colonies, and antibiotics for bacterial disease, there are no registered products available to beekeepers for reducing the impacts of chemical exposure on bee health nor for controlling viruses. Additionally, since the removal of Fumagillin-B from the market in 2018, there is no registered treatment for the control of *Nosema* fungal infections. To date, the management recommendation for honey bees with respect to pesticide exposure is simply a reduction in exposure levels by moving beehives away from agricultural settings and regulatory restrictions related to the seasonal timing of pesticide application. This policy involves extra labor and reduces both the input of nectar and pollen into beehives and the benefits of honey bee pollination for crops.

Therefore, an urgent need exists to fill current voids in honey bee health management and provide innovative solutions to improve overall bee health and prevent colony collapse. A particular urgency exists to mitigate the detrimental effects that parasites and pesticides have on honey bee colony productivity without disturbing the progress of agricultural production.

SUMMARY OF THE INVENTION

To address these challenging issues related to honey bee health and reduce population decline, this invention provides novel cyclodextrin-based compositions and methods to promote and improve honey bee health and enhance survival. The compositions are ingestible by honey bees and capable of scavenging toxic compounds from honey bees and by extension boost the immune defenses of individual honey bees and the entire colony against infectious disease and reduce the effects of pesticide exposure. In general, this invention seeks to mitigate several of the cumulative problems associated with the health of honey bee pollinators that are directly tied to agroeconomic success.

In an aspect, the invention is a composition comprising a mixture of at least one cyclodextrin, a carrier, and optionally one or more vitamins and/or nutrients. The mixture provides an effective amount of the at least one cyclodextrin to a beehive to improve at least one health factor of bees in the beehive.

In another aspect, the invention is a method of improving beehive health. The method includes administering a mixture of at least one cyclodextrin, a carrier, and optionally one or more vitamins and/or nutrients to a beehive.

In a further aspect, the invention is an apparatus comprising a feeder which allows bees in a beehive to access a mixture of at least one cyclodextrin, a carrier, and optionally one or more vitamins and/or nutrients.

It is an advantage of the invention to provide novel compositions of cyclodextrin having multi-functional properties to protect honey bee health and give bees strength to defend the hive from invasive insects.

It is another advantage of the present invention to provide novel compositions and methods to decrease pesticide toxicity towards honey bees and improve beehive health including increasing the lifespan of honey bees.

It is a further advantage of the present invention to provide compositions and methods useful for preventing and treating infectious diseases in honey bees including diseases caused by viral infections and/or the reduction of fungal spores.

It is yet another advantage of the invention to increase beehive efficiency via added days to the average lifespan of honey bees encountering pesticides that translates into more cumulative work completed by bees attending to a hive and increases in economic success shared between various sectors of the agriculture industry.

An additional advantage of the invention is to provide ingestible cyclodextrin-based compositions to improve overwintering ability in of bee colonies and promote increased economics for beekeeping annual cycles.

Yet another advantage of the invention is to provide a novel remediation-based method that mitigates the damage caused by common in-hive chemicals used to treat for mites and other insects or parasites.

A further advantage of the present invention is to provide novel formulations that include fat-soluble nutrients in an aqueous solution.

This summary is provided to introduce a selection of concepts in a simplified form that are further described below in the detailed description. This summary is not intended to identify all key or essential features of the claimed subject matter, nor is it intended to limit the scope of the claimed subject matter.

DETAILED DESCRIPTION OF THE INVENTION

Figure 1:
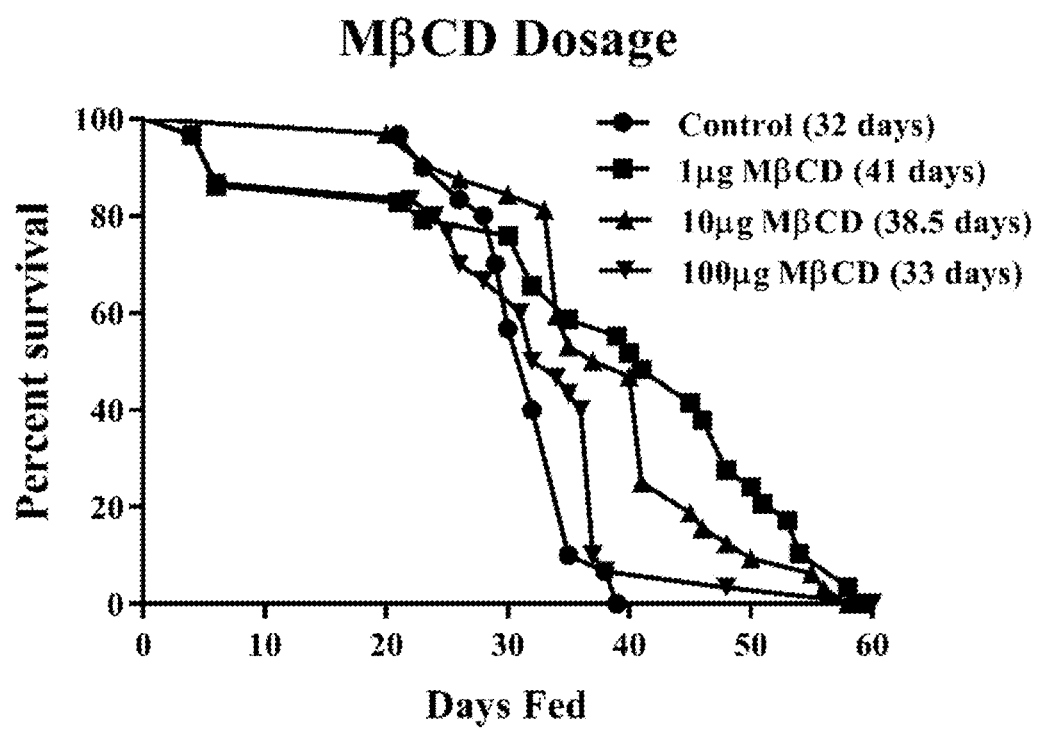
FIG. 1 illustrates dose response results for the longevity of healthy adult bees after MBCD treatment when administered to newly emerged worker bees.

Unless herein defined otherwise, all technical and scientific terms used herein generally have the same meaning as commonly understood by one of ordinary skill in the art to which this invention belongs. The definitions and terminology herein described for embodiments may or may not be used in capitalized as well as singular or plural form herein and are intended to be used as a guide for one of ordinary skill in the art to make and use the invention and are not intended to limit the scope of the claimed invention. Mention of trade names or commercial products herein is solely for the purpose of providing specific information or examples and does not imply recommendation or endorsement of such products.

As used in the description of the invention and the appended claims, the singular forms "a," "an," and "the" are intended to include the plural forms as well, unless the context clearly indicates otherwise.

The term "bee" or "honey bee" interchangeably refers to any species of bee used for performing pollination services including, for example, bees from the genus *Apis* (e.g., *A. mellifera* or *A. cerana*).

The term "beehive" or "colony" refers to either a singleton or a plurality of bees living in a natural or constructed habitation. For the latter, populations may or may not be comprised of individuals from overlapping generations and may or may not have an actively reproducing "queen" (i.e., "queen-right"). Most beekeepers maintain honey bee colonies in, for example, "Langstroth" wooden hives (or other types of structures as discussed below) with removable frames.

The term "carrier" refers to a component of the inventive composition that mimics or supplements naturally occurring nectar the bees would find and use for upkeep of the hive and mixes with the CD component without undesirable binding. This component may comprise a variety of difference substances that are an attractant and/or phagostimulant (e.g., water, natural or synthetic varieties of nectar, nectar substitutes, sugar granules, sugar dough, sugar solution, sugar substitute, etc.) that is capable of providing the CD(s) of the invention to the bees in an ingestible form. This component may also include other nutritive or non-nutritive constituents. This component preferably does not contain a pollen or pollen substitute to prevent undesirable binding of the CD component.

The term "consisting essentially of" excludes additional steps or components that substantially interfere with the intended activity of the invention and can be readily determined by those skilled in the art, for example, from a consideration of this specification or practice of the invention disclosed herein. This term may be substituted for inclusive terms such as "comprising" or "including" to more narrowly define any of the disclosed embodiments or combinations/sub-combinations thereof. Furthermore, the exclusive term "consisting" is also understood to be substitutable for these inclusive terms.

The term "cyclodextrin" or "CD" refers to a macrocyclic polysaccharide class of compounds that are typically six-, seven-, or eight-membered rings (e.g., α-CDs are six-membered, β-CDs are seven-membered, and γ-CDs are eight-membered) and contain a hydrophobic core. In general, "BCD" refers generally to β-cyclodextrins. The CD component of the inventive composition is an active ingredient and is not an excipient material. Typically, the more monomers in the macrocycle, the larger molecule may be incorporated into an inclusion complex or for sequestration. For example, BCDs generally have the correct pore size/gauge to fit tocopherols in an inclusion complex as well as sequester most classes of pesticides. Among other functional characteristics, these compounds typically are capable of binding to, for example, organophosphates (OPs), pyrethroids, formamidine, and neonicotinoid pesticide families (which have some degree of acute, chronic, or sublethal toxicity associated with honey bees). Examples of modified cyclodextrins used in the disclosed invention include methyl-β-cyclodextrin (MBCD) and hydroxypropyl-β-cyclodextrin (HPBCD), which have improved absorption (e.g., for drug delivery), while still being quite general in the types of substrates they are able to bind and sequester. It is possible to use unmodified CDs as well because they typically have similar binding potential; however, they are less soluble and may not be efficiently excreted from the bees. Modified CDs, on the other hand, tend to have greater specificity (i.e., more selective in the substrates they can sequester/bind) and have the advantage of being generally better absorbed.

The term "effective amount" of a compound or property as provided herein is meant such amount as is capable of performing the function of the compound or property for which an effective amount is expressed. As is pointed out herein, the exact amount required will vary depending on recognized variables such as the compounds employed and various internal and external conditions observed as would be interpreted by one of ordinary skill in the art. Thus, it may not be possible to specify an exact "effective amount," though preferred ranges have been provided herein. An appropriate effective amount may be determined, however, by one of ordinary skill in the art using only routine experimentation.

The term "health" or "health factor" refers to one or more measurable characteristics of a colony, such as, the longevity of worker bees, lifespan of bees or a colony, survival and fecundity of queens, overlapping generations, reduction of fungal spores, and, ultimately, the growth and survival of entire colonies.

The term "inclusion complex" refers to any combination of the CD composition of the invention combined with fat-soluble components (e.g., lipophilic substrates) or other substrates.

The term "infectious disease" refers to diseases or sicknesses caused by pathogenic microorganisms in honey bees such as Deformed wing virus, fungal infections, among others, in honey bees.

The term "optional" or "optionally" means that the subsequently described event or circumstance may or may not occur, and that the description includes instances and embodiments in which said event or circumstance occurs and instances and embodiments where it does not. For example, the phrase "optionally comprising one or more vitamins and/or nutrients" means that the composition may or may not contain a vitamin and/or nutrient and that this description includes compositions that contain and do not contain a vitamin or nutrient.

The term "spore count" refers to an amount or number of fungal spores within a honey bee. For example, the number of fungal spores (e.g., absolute total or relative number per bee, per colony, or portion of a colony) would be determined from spores counted from within the intestinal tract of a honey bee.

The term "viral load" refers to an amount or number of viruses inside of a bee and typically is an absolute or relative number of viral particles per bee. This measurement may also include viral replication capacity.

The present invention provides a solution to the high rate of bee colony collapse through several novel features that are beneficial to honey bee colony health including increased lifespan of individual bees, enhanced overall bee health, improved overwintering capacity of the bee colony, reduced pesticide toxicity, reduced viral load, reduced spore count, and other benefits as will be apparent to one skilled in the art. For example, disease-causing viral particles can gain access to the nutrients and replication machinery of the cell (e.g., via endosomes) allowing for replication within bee tissues.

In embodiments, the invention is a composition including a mixture of at least one cyclodextrin, a carrier, and optionally one or more additives to form an inclusion complex. The mixture provides an effective amount of the at least one cyclodextrin to a beehive to improve at least one health factor of bees in the beehive. As a non-toxic, eco-friendly, user-friendly, and cost-effective constituent, the CD-containing composition of the invention offers a novel and surprisingly effective solution to the major bee health challenges caused by environmental factors (e.g., pesticides, mites, fungi, viruses, etc.) and can be readily adapted into the common beekeeping practices in the U.S. and globally. Experimental results shown in the examples below illustrate the surprising and unexpected effect that feeding CD to bee colonies can significantly increase the lifespan of bees insulted with common pesticides as well as bees carrying a large load of multiple viruses. Such treatment with the inventive compositions provides a potent detoxification strategy to minimize risk by reducing hive pesticide residues and other toxins that pose major threats to the health and well-being of honey bees. Cyclodextrins are a family of compounds made up of sugar molecules bound together in a ring and are water-soluble, biocompatible in nature with a hydrophilic outer surface and a lipophilic inner cavity as well as being generally recognized as safe (e.g., used in food technology, human nutrition, medicine, etc.). Not intending to be theory-bound, it is thought that the outer surface of the CD structure provides a hydrophilic surface and a hydrophobic inner pocket rendering the molecule amphiphilic which may allow it to interact with insoluble waxy elements of the comb and aqueous elements like honey simultaneously. The cyclic structure also allows CDs to form inclusion complexes with a wide range of molecules (e.g., food additives, flavorings, stabilizers, absorbents, nutrients, vitamins, among others) and serve as a carrier to deliver those molecules to beehives and/or to sequester and thereby block the toxic activity of environmental insults, such as multiple classes of pesticides and pathogenic microorganisms.

In embodiments, the present invention utilizes one or more CDs as an active ingredient, preferably modified CDs as herein described, as a safe and capable molecule to confer protection from environmental chemical and biological threats (e.g., neonicotinoid pesticides that are highly toxic to bees, viral loads, spore count, etc.) thereby extending the lifespan of bees. The cyclodextrin component of the inventive mixture is preferably a modified CD (such as the BCD versions MBCD or HPBCD) but other CDs may also be used according to alternative embodiments. Preferred BCD compounds include methyl-ß-cyclodextrin (a methylated form of cyclodextrin) and hydroxypropyl-ß-cyclodextrin (a hydroxypropylated form of cyclodextrin). It should be appreciated that particular CDs are selected for use in the inventive compositions because of their ability to maintain higher levels of absorption while retaining a wide range of binding partners. The inventive CD-containing compositions are readily consumed by honey bees and provide significant and surprisingly unexpected increases in lifespan as well as a protective effect against potentially harmful biotic and abiotic threats such as pesticides, agrochemicals, viruses, cold weather, and possibly habitat loss and degradation, climate change, etc. Not intending to be theory-bound, with respect to certain chemical threats a protective mechanism of action of CDs ingested by bees might be that the cyclodextrin class of compounds sequester toxic molecules (e.g., neonicotinoids, pyrethroids, organophosphates, etc.) used in the agricultural industry which reduces the toxicity of such compounds against the bees. As an active ingredient, CDs may also accelerate autophagic flux to aid in the clearance of fungal spores from bees. Modified CDs may also shield bees from the chronic and sub lethal effects posed by in-hive applied acaricides such as amitraz.

The inventive mixture preferably also includes a carrier for the CD in the form of a nutritive or non-nutritive component that is attractive to bees (e.g., an attractant and/or phagostimulant) and promotes ingestion of the mixture and that does not interfere with the functionality of the inventive mixture in bees. The carrier may be in the form of an aqueous solution, a syrup, a solid, a spray, a dough, a granule, a powder, a gel, and combinations thereof. It should be appreciated that the carrier may generally be used at any concentration as determined by a skilled artisan. In preferred embodiments, there is from about a 1:1 to about a 1:2 ratio of $H_2O:CHO$ (e.g., sucrose and water or sugar syrup) maintained in solutions because this range tends to be the most attractive to bees. With the carrier, the inventive mixture is formulated such that it is attractive to and easily consumable and ingestible by bees. It should be appreciated that water could also be used as a carrier but the bees would take it more slowly, and as an upper limit sugars generally become cumbersome to work with after about 80 wt % in aqueous solution. Preferred formulations for the mixture include, for example, honey bee dietary syrup (e.g., liquid or emulsion), spraying (e.g., aerosols or non-aerosols, air gun, electrostatic spray, electric fan, airless spray, automated linear spray, automated flat line spray, booth spray, etc.), and strips that the bees are able to chew through to access and ingest the inventive composition (e.g., pulp-based material strips, paper-based, wax-based, etc.) within a commercial colony or beehive. Dietary syrups are generally preferred and typically provide the most robust and simplest means for application, and is the predominant practice employed by beekeepers. The carrier acts to attract the bees and ensures they feed on the composition of the invention to maintain an adequate dosage and pharmacokinetics of the one or more CDs within the bee population to ensure maximum effectiveness of the inventive composition. There is no general preferred recipe for the carrier, but most nectar substitute compositions comprise ingredients such as soy flour, sugar, yeast, sugar syrup, and/or honey. One method forming MBCD, for example, may be synthesized by reacting BCD with methyl-halogen (M-bromide/M-iodide) in the presence of a strong acid. A newer "greener" synthetic pathway using BCD, dimethyl carbonate, anhydrous potassium carbonate, and dimethyl fluoride has also been described semi-recently (see e.g., Zhang et al., 2011). Another more general review on the organic synthesis of CDs is known as well (see e.g., In book: Cyclodextrin Fundamentals, Reactivity and Analysis, Synthesis of Cyclodextrin Derivatives, Rezanka, 2018, pp. 57-103). MBCD and HPBCD in the form used in the inventive composition is also commercially available from, for example, SigmaAldrich (St. Louis, Mo.) or Fisher Scientific International, Inc. (Hampton, N.H.).

In embodiments, the inventive composition further comprises one or more vitamin (e.g., vitamin A, vitamin $A_1$ or retinol, vitamin D, vitamin $D_2$ or ergocalcitriol, vitamin E or tocopherols, etc.), mineral, nutrient, fat-soluble components, or other components as selected by a skilled artisan to provide additional nourishment and/or health benefits for the bee colony. Such other components may be present in effective amounts for the particular component selected. In addition, a skilled artisan would select the components for needs associated with the particular application. Selection criteria may include factors such as dietary and nutritional needs, viral load issues, mite infestations, bacterial contamination, fungal contamination, and the like as well as combinations thereof.

In embodiments, the concentrations of the components used for the inventive composition are sufficient to deliver an effective amount of the desired components to a beehive to improve at least one health factor of bees in the beehive or colony. For example, Table 1 sets forth concentration ranges for the ingredients of the inventive compositions for use in the methods of the invention (to be interpreted as having "about" preceding the values) to encompass various embodiments as described herein.

TABLE 1

| Ingredient | Broadest | Broad | Intermediate | Narrow |
| --- | --- | --- | --- | --- |
| Carrier | 0-80 wt % | 20-70 wt % | 30-60 wt % | 50 wt % |
| CD | 0.04-4 g/L | 0.08-2 g/L | 0.16-1 g/L | 0.45 g/L |
| Tocopherol | 0.1-4 µg/L | 1-4 µg/L | 2-4 µg/L | 4 µg/L |
| Retinol | 0.13-2.4 mg/L | 0.75-2 mg/L | 1-1.5 mg/L | 1.3 mg/L |
| Ergocalcitrol | 1-20 µg/L | 10-175 µg/L | 100-150 µg/L | 150 µg/L |

In embodiments, the inventive composition comprises tocopherol. Tocopherols generally aid in providing nutrition for the bees buy may also have other beneficial effects. Though various tocopherols may be used, highly active isomers of the tocopherol-tocotrienol family are preferred. It should be appreciated that if a tocopherol with lower activity or efficiency is selected, the employed concentrations would need to be adjusted accordingly by a skilled artisan. One example of a highly active tocopherol isomer is (+)-α-tocopherol (e.g., CAS No. 59-02-9) and a lesser active version is CAS No. 10191-41.0 (both available from Sigma Aldrich, St. Louis, Mo.). In embodiments, the inventive composition comprises retinol and/or ergocalcitriol. It should be appreciated that the inventive composition may include any combination of tocopherol, retinol, an/or ergocalcitriol as determined by a skilled artisan for a particular application of the invention.

In embodiments, one or more of the additional component(s) are part of an inclusion complex including at least one cyclodextrin and at least one other component. Other components for such embodiments are generally fat-soluble components and the inclusion complex allows the fat-soluble components to be incorporated into the inventive composition. The inclusion complex is used for solubilizing and stabilizing compounds that are otherwise insoluble in water (e.g., tocopherols, vitamins A, D, K, etc.). An inclusion complex may be created in a number of ways to incorporate fat-soluble components into inventive composition as may be determined by a skilled artisan (see e.g., Celebioglu et al., 2017). As a general example of an inclusion complex, approximately 9 g to 10 g of a CD/tocopherol complex is mixed into 10 gallons of an approximately 50% sucrose solution (e.g., sucrose or sugar syrup). The tocopherol is preferably present in the final formulation in an amount ranging from about 2 mg (μL) 1000 U/g vitamin E per 3.785 L to about 20 μL of vitamin E included into from about 900 mg to about 9000 mg of CD is sufficient to make about 10 gallons of the inventive composition as a formulation that is ready to apply.

In embodiments, the total concentration of CD(s) in the mixture is adjusted to provide from about 2 μg to about 200 μg, or from about 2 μg to about 100 μg, or from about 2 μg to about 50 μg, or from about 2 μg to about 20 μg, or about 10 μg per bee in the beehive per month. For a typical hive, the amount of CD active ingredient the inventive compositions would provide in total for the hive or colony would be broadly from about 2 mg to about 20 g, or from about 2 mg to about 10 g, or from about 2 mg to about 5 g, or from about 100 mg to about 2 g, or about 1 g per month. The delivered dosage in terms of the CD active ingredient to beehives is in the range of about 100 mg to about 1 g per month per colony. In embodiments with tocopherol, the amount of tocopherol provided in the inventive compositions per bee in a hive or colony is broadly from about 1 international unit (IU) to about 60 IU or from about 2 IU to about 50 IU, or from about 2 IU to about 40 IU, or about 20 IU, or about 40 IU per 7.7 L sugar solution per month. For a typical hive, the amount of tocopherol in the inventive compositions would provide in total for the hive or colony would be broadly from about 0.04 mg to about 0.06 mg, or at least about 0.04 mg per 7.7 L sugar solution per month.

An exemplary method of preparing the inventive composition includes using powdered BCD and adding (e.g., pipetting) tocopherol oil into the powder. Upon vigorous mixing by kneading, grinding, vortexing, shaking, etc., the oil will be incorporated into the dry BCD powder to form an inclusion complex and will have the appearance of a dry powder again. The oil may alternatively be placed and left in the powder (e.g., with overnight refrigeration) and will transform into an inclusion complex. Tocopherol oil is generally dark brown in nature but when it is included in the BCD rings, the powder typically turns to white off-white in color. The BCD-tocopherol inclusion complex may then be mixed into the sugar syrup to create a usable formulation, typically with a noticeable amount of foam and froth at the top of the mixture. The BCD-tocopherol powder may also be mixed with solid sugar, and then water added to create a solution for application. Formulations of the inventive compositions may vary in concentration of the CD component depending on the application. For overwintering success, for example, involves adding broadly from about 1 μL to about 50 uL, more specifically from about 10 μL to about 30 uL, or about 20 uL of tocopherol (e.g., 1 IU/μg) into broadly from about 1 g to about 20 g, more specifically from about 5 g to about 15 g, or about 10 g of HPBCD and kneading/vortexing/mixing until tocopherol is fully included and returns to white to light brown/yellow powder. HPBCD-tocopherol is then dissolved in broadly into about 3.785 L to about 154 L, more specifically from about 18.93 L to about 77 L, or about 37.859 L (i.e., about 10 gallons) 50% sucrose solution. The resultant solution is administered at broadly from about 0.3785 L to about 19 L, more specifically from about 0.77 L to about 7.7 L, or about 3.785 L per colony per 2 weeks. In another example, formulations for short term *Nosema* treatment involve adding broadly from about 0.001 mg/L to about 2 mg/L, more specifically from about 0.13 mg/L to about 2 mg/L, or about 1.3 mg/L retinol and broadly from about 0.15 μg/L to about 300 μg/L, more specifically from about 15 μg/l to about 200 μg/L, or about 150 μg/L ergocalcitriol into broadly from about 87 mg/L to about 2 g/L, more specifically from about 200 mg/L to about 1 g/L, or about 870 mg/L MBCD and kneading/vortexing/mixing until the retinol and ergocalcitriol are fully included and return to a white to light green/yellow powder. MBCD-retinol-ergocalcitriol is then dissolved in broadly from about 0.1 L to about 1 L, more specifically from about 0.25 L to about 0.75 L, or about 0.5 L sucrose solution, and administered at about 0.5 L per colony per 2 weeks. It should be appreciated that mixing times for preparation may vary and be determined by a skilled artisan depending on the particular components and batch size.

In embodiments where the mixture is in a liquid form, honey bee colonies typically require from about 1 liter to about 4 liters of the mixture if administered in solution form approximately every 2 weeks depending on the size of the colony. For example, 10 gallons of the mixture in a liquid syrup form is sufficient to feed between approximately 10 and 40 honey bee colonies every 2 weeks depending on the populations. To provide desirable dosage levels and maintain duration of effect in the honey bees, the effective concentration ranges for the CDs in the mixture are from about 20 mg/L (e.g., about 90 mg/gal) to about 250 mg/l (e.g., about 900 mg/gal). By way of example, the inventive composition may be formulated to feed approximately 20 beehives with a half-gallon once per month and is about 5× more concentrated than the solution normally used in the laboratory trials (see examples below). The reasoning behind this higher concentration for field use is an estimation that some percentage of the CD will be lost to the environment (e.g., diluted with nectar and/or pollen brought into the hive by bees) when applied to a honey bee colony/hive. Additionally, 10× less of this concentration was found to not be very effective, and 10×higher concentration was found to be no more effective and begins to demonstrate toxic effects. In an embodiment of a solid or granular form of the inventive composition, a dry (i.e., cake-like) or fondant (i.e., cooked sugar-like) treatment for example, about 11 kg of sugar would be vigorously mixed with about 3 g to about 9 g of HPBCD, then about 1.5 L of water would be added. The mixture would be spread in a pan and allowed to dry overnight (or heated to produce fondant candy). This "cake" could be cut to provide broadly 2.5 kg to 12 kg, more specifically about 4 kg to about 6 kg, and discreetly about 4 kg of granule/solid per colony per about 1 to about 3 months.

In embodiments, a liquid form of the composition is mixed into a syrup in small or large batches and pump-fed into one or a plurality of colonies or hives via a powered pump or may also be manually administered or poured as determined by a skilled artisan. In embodiments, the composition of the invention is placed in an apparatus comprising a feeder for supplying the inventive mixture to honey bees in a beehive. The feeder is operable to store an amount of the inventive composition and provide the composition to the bees for a prescribed period of time at a prescribed dosage and is preferably reloadable and accessible from outside the bee colony. In embodiments, the apparatus is also operable to deny access to antagonistic insects. The feeder used for the apparatus may include one or more feeders as selected by a skilled artisan. The selected feeders may be designed specifically for the composition of the invention or may include known feeders in the art. For example, the feeder may include one or more selected from a community feeder; a Boardman entrance feeder; a gravity fed waterer; a double hive top feeder; a quad hive top feeder; a round top feeder; a pollen syrup top feeder; a division board feeder; a bucket feeder; and combinations thereof. In embodiments, the feeder is operable to deny, preclude, or reduce access to antagonistic insects or pests. It is generally beneficial to prevent the inventive composition from being exposed to sunlight to ensure the components do not prematurely breakdown. As such, internal feeders or feeders that prevent sunlight exposure are desirable.

There are different kinds of feeders that beekeepers use to provide food to colonies when nectar is in short supply or unavailable. For example, an entrance feeder might be used to deliver the inclusion complexes dissolved in sugar syrup. An entrance feeder sits at the entrance to the beehive and is comprised of a feeding tray that goes on the entrance of the hive and an inverted container holding solution. The bees feed through the access holes in the jar lid. One advantage of the entrance feeder is to avoid the pests that prey in a totally dark environment of bee hives. In addition, the level of solution remaining is visible to a beekeeper from outside the hive, avoiding the need to open the beehive to check feed levels. There are also entrance feeders that are fillable without disturbing the honey bee colony. In embodiments, if a large "batch" of the inventive composition was desired, the packaging would include a sealed packet (e.g., dark brown plastic to protect from light) of compounds for 1 to 50 hives (e.g., about 1 g to about 50 g), 50-500 hives (e.g., about 50 g to about 500 g), or 500+ hives (e.g., about 500 g+) to be mixed thoroughly in sugar water (e.g., 0.0001%-99.9% sugar in water) and administered at between about 3.785 L to about 19 L per top box feeder.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from error found in their respective measurement. The following examples are intended only to further illustrate the invention and are not intended in any way to limit the scope of the invention as defined by the claims.

Example 1

This example illustrates the baseline effects of the inventive composition in the absence of an exogenous stressor. Samples of European honey bees, *Apis mellifera*, were collected from colonies maintained in the apiaries of the USDA-ARS Bee Research Laboratory in Beltsville, Md. Frames with emerging brood were removed from colonies and individually placed in a mesh-walled cage. The cages were transferred to an insect growth chamber at 34° C. and 70% humidity. After 24 hrs incubation, newly emerged honey bees were transferred to a honey bee rearing cup, with a top-feeder design, allowing for easy sampling of honey bees (see e.g., Evans et al., 2009). A 3 mL syringe filled with 50% sugar syrup mixture was inverted over the top of the rearing cup to provision the caged honey bees. The honey bees were also provisioned with 1.5 grams of honey bee pollen supplement in patty form (e.g., Bee-Pro®, available from Mann Lake Ltd, Hackensack, Minn.), supplemented 10% (w/w) with ground fresh pollen, and placed on cotton paper on the cup cage bottoms. Syringes and sucrose solution were changed every 3 days and cotton paper was changed once per week.

This example demonstrates that treatment of healthy adult worker honey bees with MBCD acts to extend the lifespan of the bees and is absent of any measured negative effects (e.g., shortened lifespan) associated with its application. Newly emerged honey bees were placed in individual cages (n=30 bees per cage & 2 replicate cages per treatment) and fed using a syringe filled with 50% sucrose alone or supplemented with either 1, 10, or 100 µg MBCD per bee/per week. It was observed that honey bees fed with 1 µg and 10 µg MBCD showed a significant increase in median lifespan of 9 and 6.5 days respectively (FIG. 1), suggesting that the use of this compound is safe for bees and surprisingly increases observed lifespan. The upper limit for CD dosage appears to be about 100 g/bee based on the observed diminishing effects. Median survival is represented for each treatment by (# days). Curves were compared using Log-Rank Mantel-Cox (p<0.0001 for Control versus 1 or 10 µg MBCD), and Gehan-Breslow-Wilcoxon (p<0.001 for Control versus 1 or 10 µg MBCD) tests.

Example 2

In this example, whether MBCD mitigates the toxicity of certain pesticides associated with honey bee death was investigated. Not intending to be theory-bound, it was hypothesized that the binding of hydrophobic pesticide molecules to CDs would translate into health benefits to honey bees that were exposed to such pesticides. Samples of honey bees were collected as in example 1. A cage study (n=30 bees per cage & 2 replicate cages per treatment) was performed using 50% sucrose solution that had been spiked with sublethal doses of common pesticides that are known to be toxic to honey bees to measure the ability of treatment MBCD compositions to confer protection to the honey bees. Analytical grade standards of clothianidin, imidacloprid, and chlorpyrifos (available from MilliporeSigma, St. Louis, Mo.) were first dissolved in acetone, then diluted to their final concentrations (Table 2) in 50% sugar syrup. The listed sublethal doses were derived from taking half of the previously published honey bee LD50s (referred to a "LD25" in Table 2). The solutions were administered via 3 mL syringes in rearing cups as previously stated. Fresh pesticide solutions were mixed every 3 days to coincide with syringe replacement (see e.g., Williamson et al., 2013; Li et al, 2017).

TABLE 2

Pesticide Dosage

| Insecticide | Class | Sublethal LD25 | Reference |
|---|---|---|---|
| Chlorpyrifos | OPs | 0.43 ng/bee | Williamson et al. |
| Clothianidin | Neonicotinoid | 1.0 ng/bee | Li, et al. |
| Imidacloprid | Neonicotinoid | 4.3 ng/bee | Li, et al. |

Figure 2A:
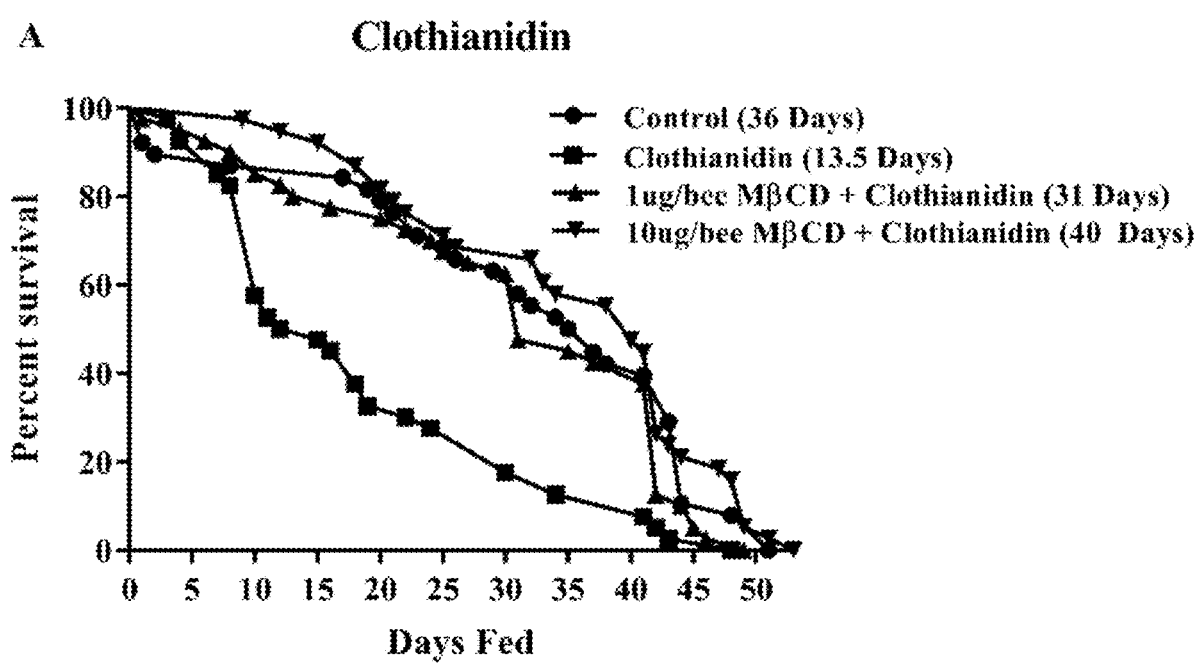
FIG. 2A to 2C illustrates dose response results for the longevity of healthy adult bees after various CD treatments when administered to newly emerged worker bees in the presence of the indicated lethal pesticides.
Figure 2B:
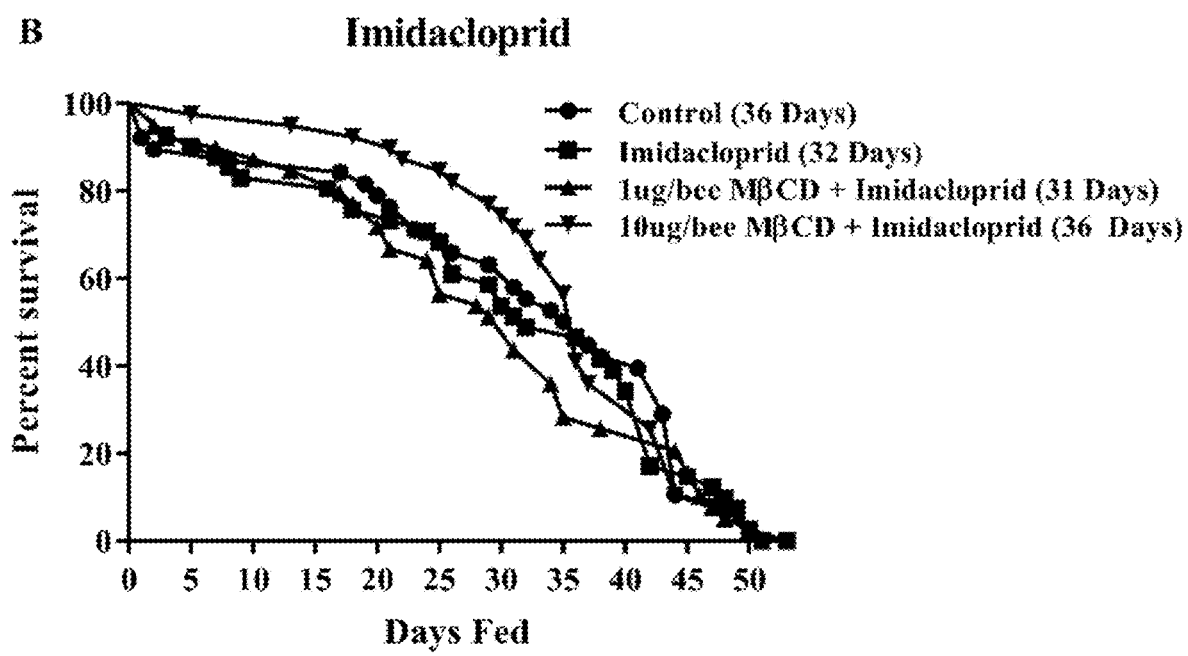
Figure 2C:
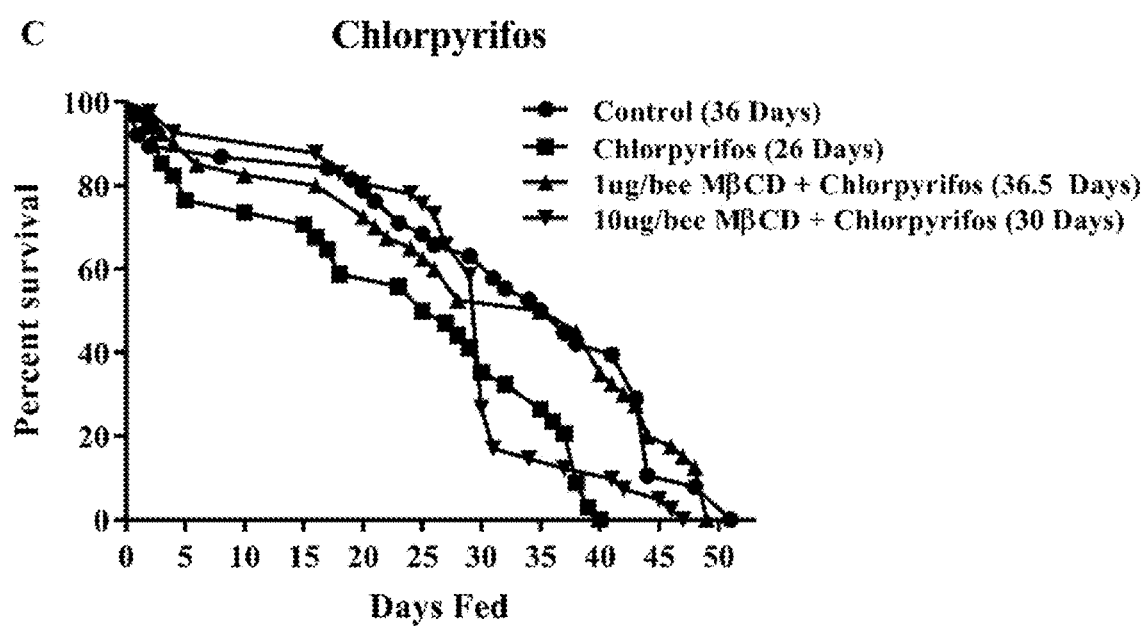

Survival curves for bees insulted with clothianidin, imidacloprid, and chlorpyrifos are shown in FIG. 2A to 2C. Median survival is represented for each treatment by (# days). Curves were compared using Log-Rank Mantel-Cox ($p<0.0001$ for clothianidin versus control, 1, or 10 µg MBCD; $p<0.001$ for chlorpyrifos versus control or 1 µg MBCD) and Gehan-Breslow-Wilcoxon ($p<0.0001$ for clothianidin versus control, 1, or 10 µg MBCD; $p<0.05$ for chlorpyrifos versus control or 1 µg MBCD). Similar results were observed for a dosage comparison of 2 µg or 20 µg MBCD (data not shown). As illustrated in FIG. 2A, positive control bees fed on clothianidin alone fared the worst of all treatments with a median lifespan of only 13.5 days compared to 36 days of the control treatment. Addition of 1 µg/bee MBCD provided some degree of protection and the median lifespan was increased significantly to 31 days. A dosage of 10 µg/bee MBCD provided the greatest protection and surprisingly extended the median lifespan to 40 days. In the case of imidacloprid, control fed bees (36 days) did not significantly differ in lifespan to that of bees fed only imidacloprid (32 days), 1 µg/bee MBCD (31 days), or 10 µg/bee MBCD (36 days) (FIG. 2B). The chlorpyrifos treatment was able to reduce median lifespan on its own to 26 days compared to the 36 days of the control (FIG. 2C). While a dosage of 10 µg/bee MBCD did increase median lifespan to 30 days, there was not a significant change in median lifespan. However, a lower dosage of 1 µg/bee MBCD surprisingly showed (36.5 days) a statistically comparable median lifespan to that of the control (FIG. 2C).

Figure 3:
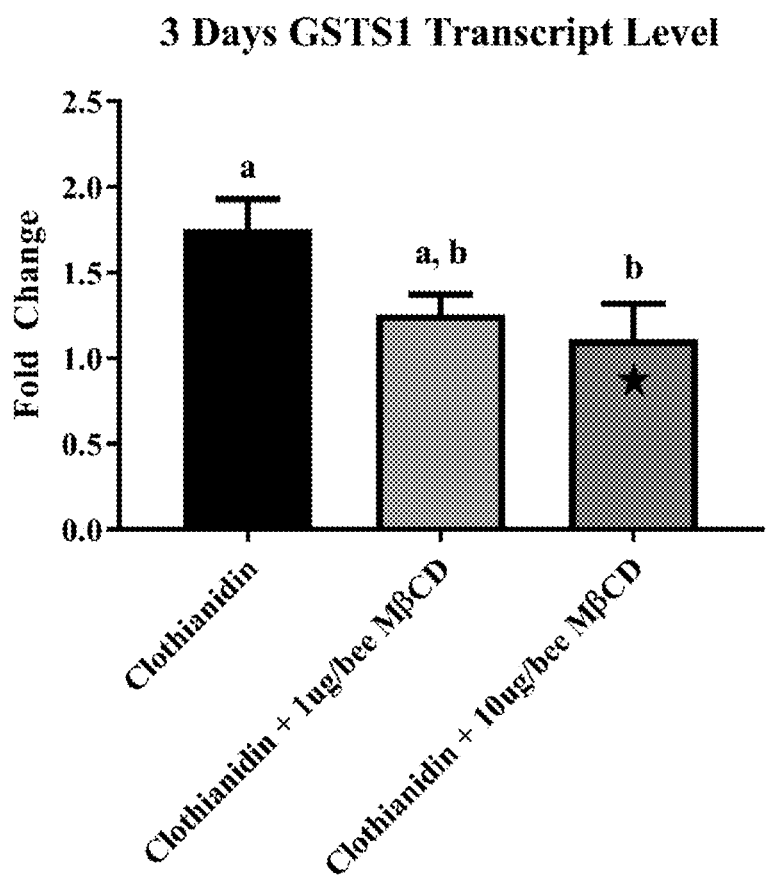
FIG. 3 shows transcript levels for the honey bee detoxification gene as an MBCD dose response.

Transcript levels for the honey bee detoxification gene glutathione-S-transferase S1 (GSTS1) showed a surprising and significant 1.5-fold decrease for bees treated with clothianidin plus 10 µg/bee MBCD compared to bees receiving only the pesticide (FIG. 3). Bees receiving clothianidin were compared to bees receiving the pesticide with the addition of 1 µg or 10 µg/bee MBCD after 3 days of feeding. One-way ANOVA with Tukey multiple comparisons was performed to determine any statistical significance ($p<0.05$ for Clothianidin versus Clothianidin+10 µg/bee MBCD). The "*" denotes the sample chosen as the $2^{-\Delta\Delta CT}$ calibrator. The reduction in GST1S transcript level suggests pesticide sequestration via CD exposure. Pesticides removed from the immediate environment results in less energy dedicated to detoxification and excretion.

Example 3

Figure 4A:
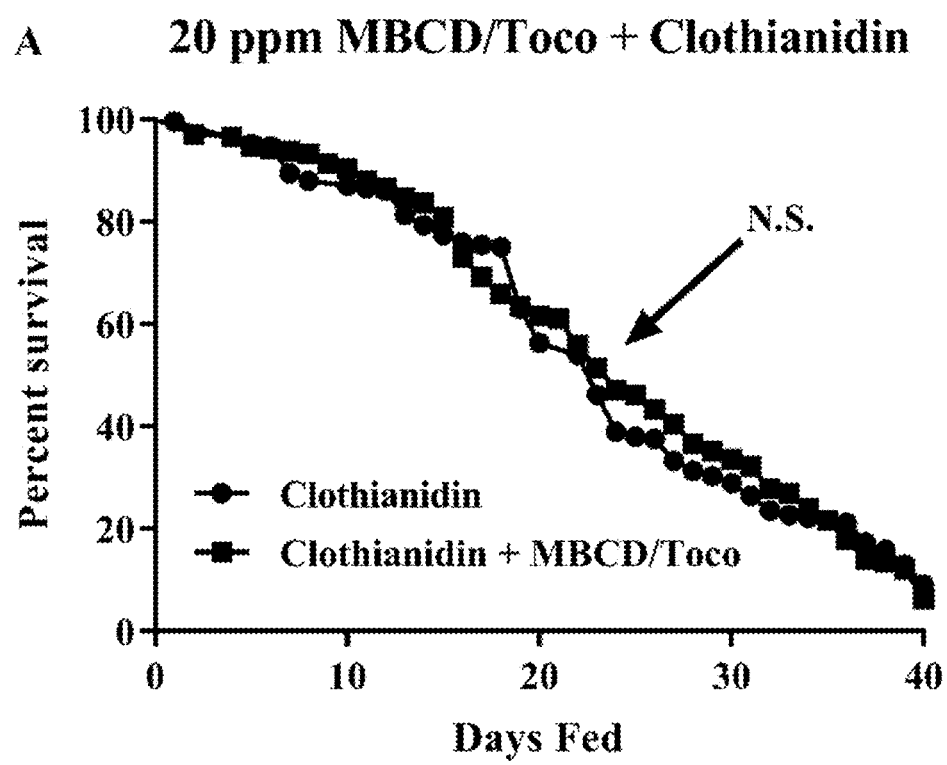
FIG. 4A to 4C illustrates MBCD & HPBCD alpha-tocopherol inclusion complex treatment for bees exposed to the indicated lethal pesticides.
Figure 4B:
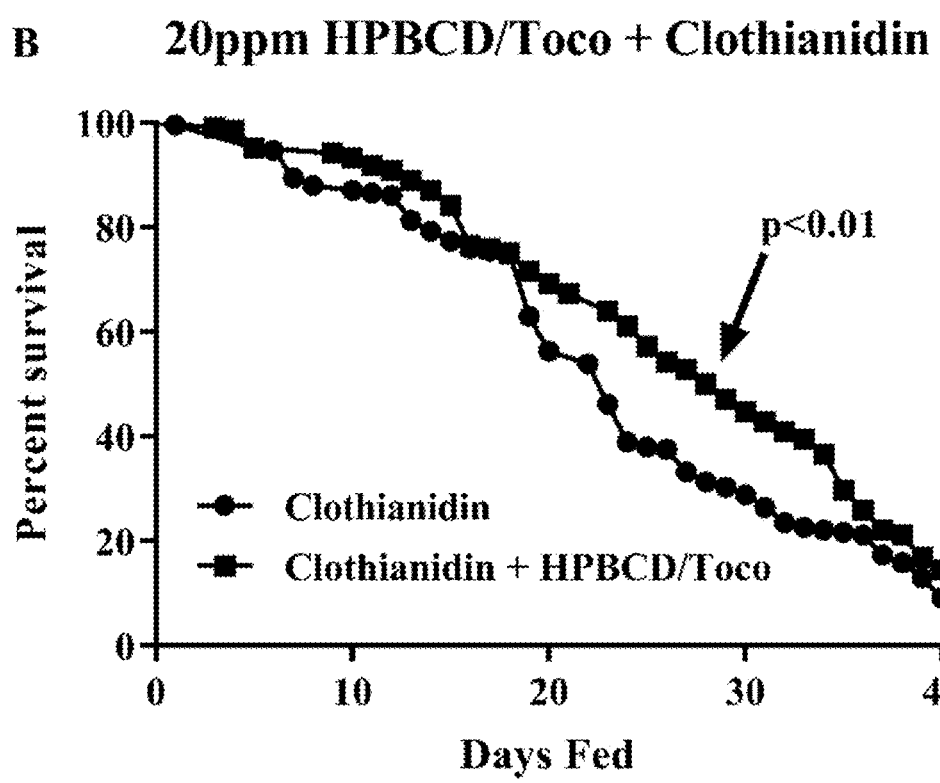
Figure 4C:
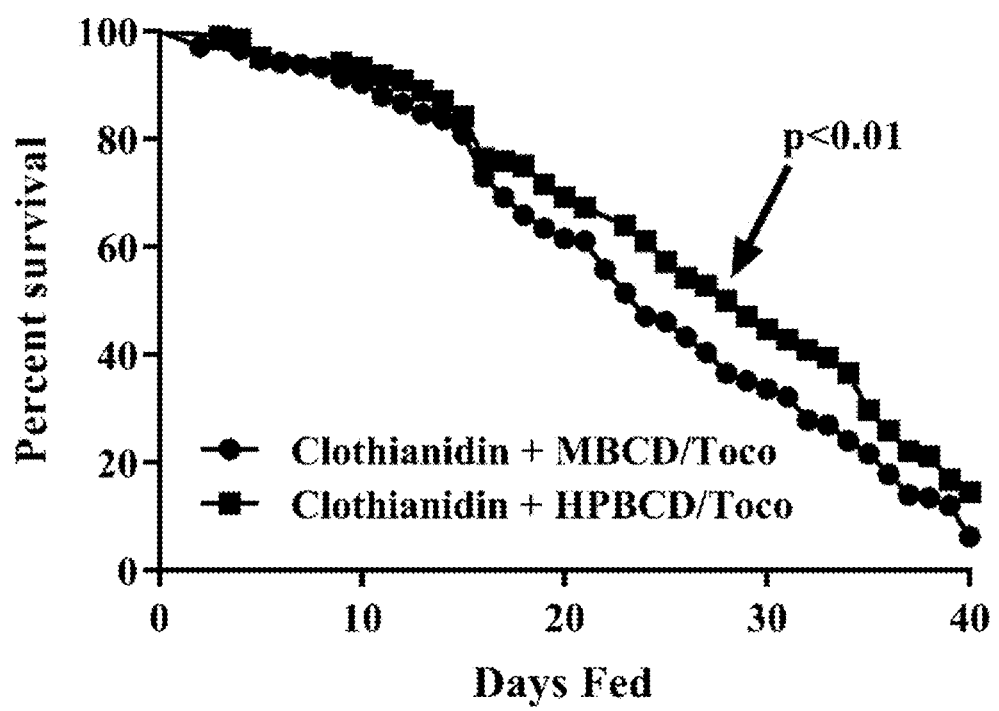

MBCD & HPBCD alpha-tocopherol inclusion complexes were formulated using 2.33 µL of +-(α)-tocopherol (1,000 I.U., available from MilliporeSigma, St. Louis, Mo.) added to 1 g of MBCD or HPBCD to arrive at a concentration of approximately 20 I.U. of tocopherol/bee/day and 10 µg (or other indicted dosage) of BCD/bee/day. The resulting powder can be stored at −20° C. or immediately dissolved into 4.166 L of water containing 50% sucrose. The resulting solution is stable and stored at 4° C. until further use. The comparative effects of MBCD versus HPBCD treated bees are shown for lab-controlled environment (n=280 bees/treatment). In FIG. 4A, it was demonstrated that while clothianidin treatment results in stunted median lifespan (22 days); 20 ppm MBCD/tocopherol complexes were capable of non-significantly (N.S.) extending the lifespan of bees (23 days; red). In FIG. 4B, HPBCD/tocopherol demonstrated a protective effect (5.5 days median lifespan) when administered at 20 ppm/bee in the presence of clothianidin only (Mantel-Cox Log-Rank $p<0.05$; Gehan-Breslow-Wilcoxon test $p<0.01$). Surprisingly, as shown in FIG. 4C, it was observed that protection from 20 ppm HPBCD/tocopherol clothianidin treated bees was more efficient than 20 ppm MBCD/tocopherol clothianidin treated bees by 4.5 days median lifespan (Mantel-Cox Log-Rank $p<0.01$; Gehan-Breslow-Wilcoxon test $p<0.01$).

Example 4

Figure 5:
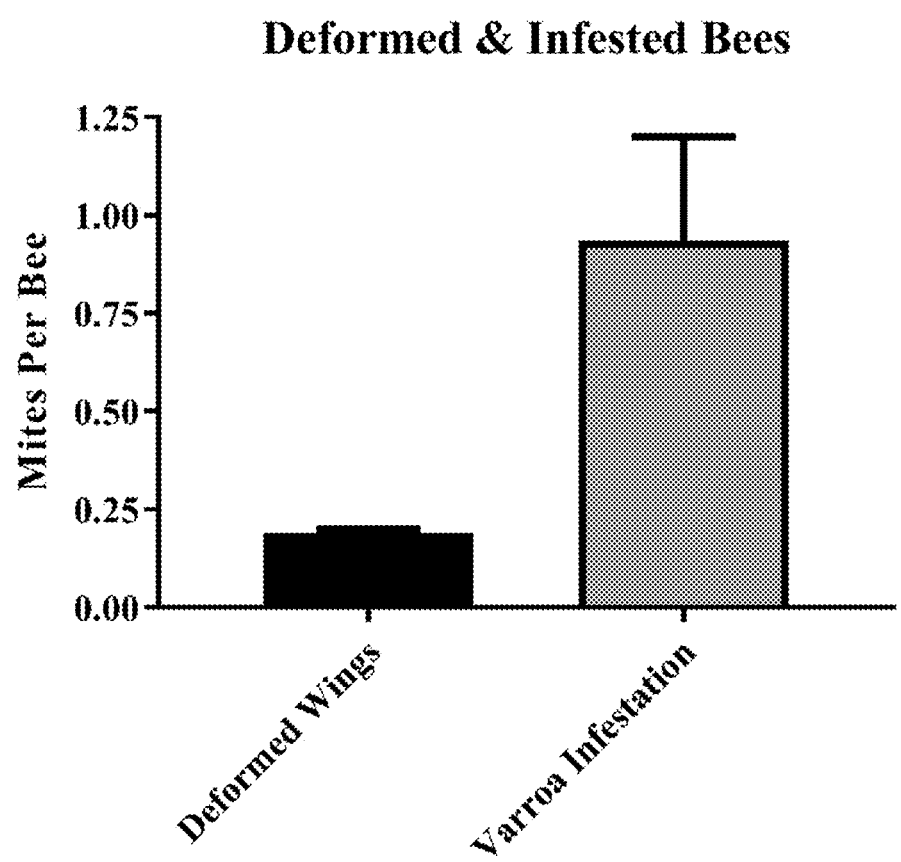
FIG. 5 shows the percentage of emerging bees with deformed wings or viral infection.

This example demonstrates honey bee survival was increased while viral titer and replication were surprisingly reduced by the presence of MBCD. Newly emerged bees were consecutively collected (2 days, n≈1000) from hives that displayed an approximately 20% Deformed wing virus (DWV, a single-stranded RNA virus or +ssRNA) symptoms and were approximately 100% infested (~1 mite/bee) with the parasitic mite *Varroa destructor* (FIG. 5). The presence of DWV and *Varroa destructor* was determined as follows. Total RNA was extracted from whole body 12 individual honey bees using the TRIzol Reagent® (available from Thermo Fisher Scientific, Waltham, Mass.) by manufacturers specifications, and stored at −80° C. First-strand cDNA was synthesized using the Superscript III Reverse Transcriptase (available in a kit from Thermo Fisher Scientific). Briefly, each reaction contained: 3 µl total bee RNA (~1 µg/µl), 1 µl of 10 mM dNTPs, 1 µl random primers (0.15 µg/µl), 1 µL of Oligo$_{(dT)}$, 1 µl of 0.1 M DTT (0.1 M), 4 µl 5×First-Strand Buffer, 1 uL of 200 U/µL RnaseOUT, 1 µl of 200 U/µl SuperScript III Reverse Transcriptase, and 7 µl Nuclease-free water. The reaction mixture was incubated at 25° C. for 5 min, 55° C. for 2 hrs, and 70° C. for 15 min, then stored at −20° C. until use. Transcript levels (RT-qPCR analysis) were quantified using the Brilliant III Ultra-Fast SYBR Green® QPCR Master Mix (Agilent Technologies, Inc., Santa Clara, Calif.) on a CFX384 Touch Real Time PCR Detection System (Bio-Rad Laboratories, Inc., Hercules, Calif.). Samples were incubated at 95° C. for 5 min, followed by 40 cycles of 95° C. for 20 s, 59° C. for 20 s, and 72° C. for 20 s. Thereafter, a melt curve analysis from 65° C. to 95° C. was performed to confirm product specificity. For the detection and quantification of negative stranded bee viruses, replication intermediates, TAG-DWV primers were substituted for random primers or oligos (see e.g., Boncristiani et al., 2009). The fold difference in viral concentration among different treatment groups was determined using the comparative Ct method ($2^{-\Delta\Delta CT}$ method) (see e.g., Livak & Schmittgen, 2001). Calibrators were chosen as the highest average treatment ΔCt value for each experiment.

Figure 6A:
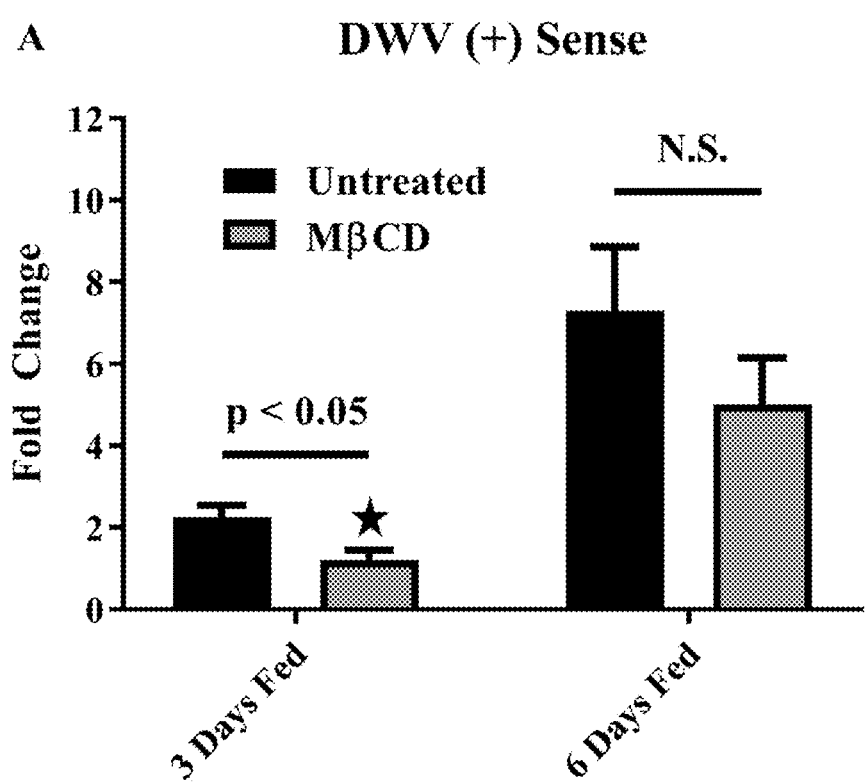
FIG. 6A to 6C show dose response viral load data for MBCD treatment related to virus-infected honey bees.
Figure 6B:
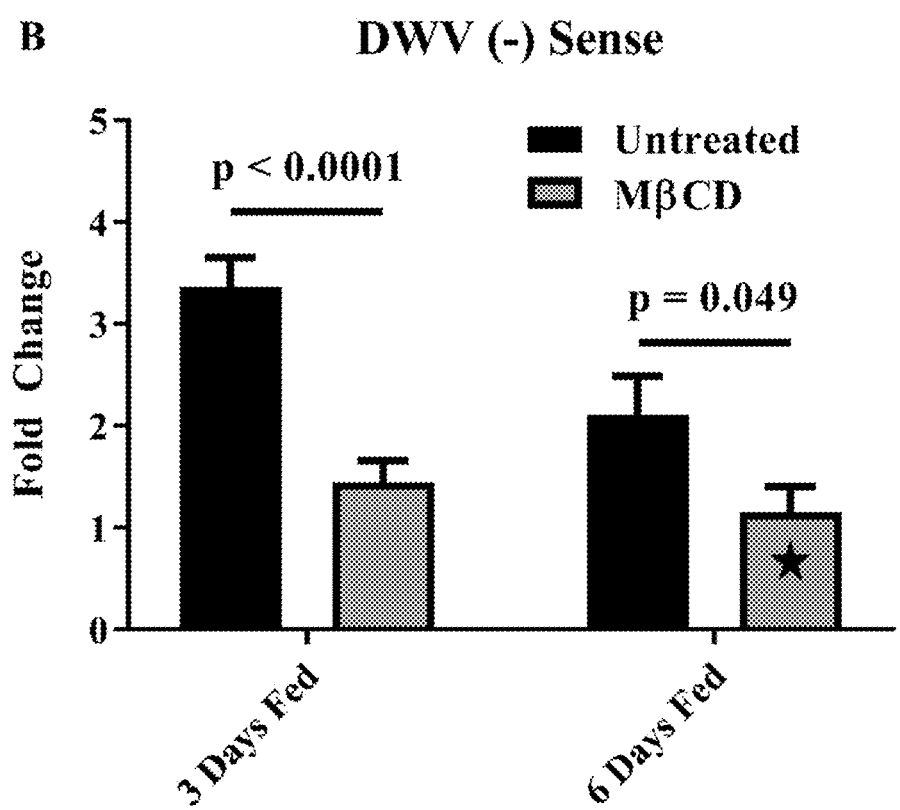
Figure 6C:
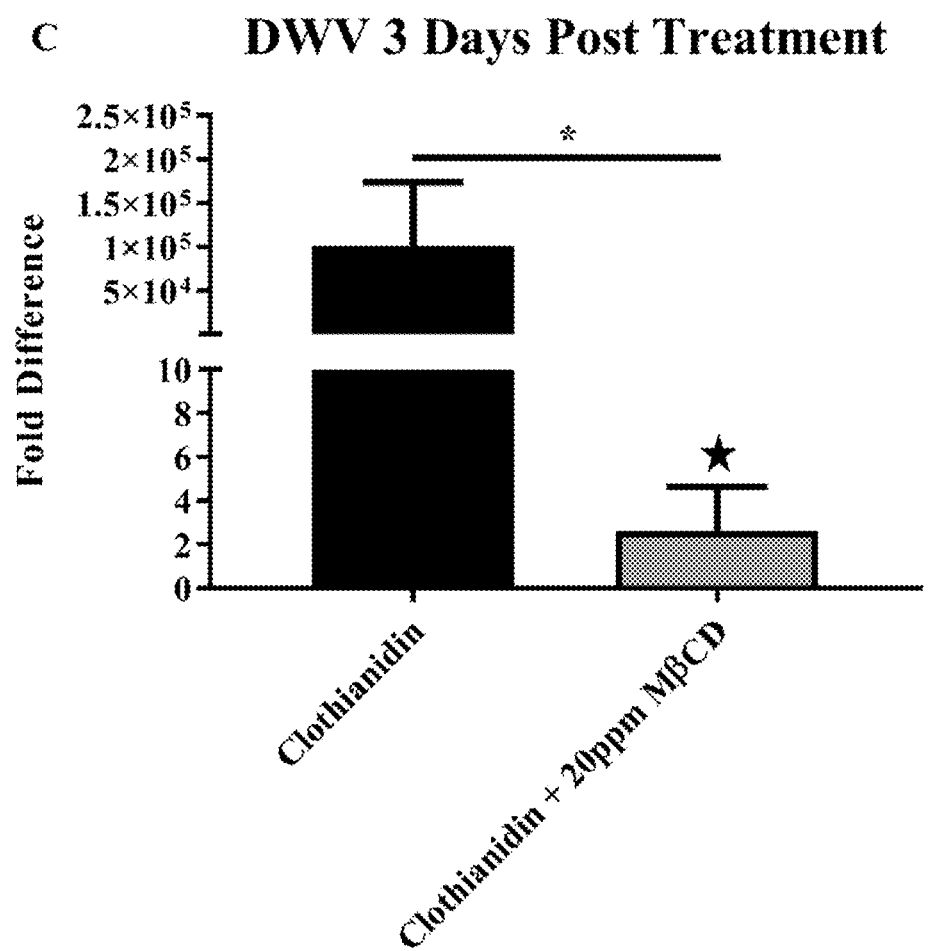

Emerging bees that had non-deformed wings (i.e., asymptomatic) were selected for a cage study (n=30 bees per cage & 6 replicate cages per treatment). DWV was observed to be the predominant virus and the positive sense viral DWV genome was detected at all time points; however, an approximate 2-fold decrease in viral genome 3 days after MBCD treatment, and a non-significant decrease 6 days post treatment was also observed (FIG. 6A). The negative sense replicative strand was not detected in newly emerged bees (Table 2), but a significant decrease was observed for 3- and 6-days post treatment (FIG. 6B; approximately 3 & 2-fold respectively). Virally infected untreated bees were compared to bees fed 10 μg/bee MBCD in 50% sucrose solution. In FIG. 6A, DWV (+) sense viral genome titers were compared 3 and 6 days after treatment. An unpaired, 2-tailed Student's T-Test was performed to determine statistical significance ($p<0.05$ at 3 days feeding; N.S.=Non-significant 6 days after treatment). In FIG. 6B, DWV (−) sense replicative strand titers were compared 3 and 6 days after treatment. An unpaired, 2-tailed Student's T-Test was performed to determine statistical significance ($p<0.0001$ for 3 days post treatments; $p=0.049$ for 6 days post treatment). The "★" denotes the sample chosen as the $2^{-\Delta\Delta CT}$ calibrator and bars denote standard error. These data suggest that MBCD is surprisingly able to limit viral replication in honey bees in vivo. Clothianidin treated bees also demonstrated higher levels of DWV compared to bees supplemented with 20 ppm MBCD (Student's t-test $P<0.05$) as seen FIG. 6C.

Figure 7:
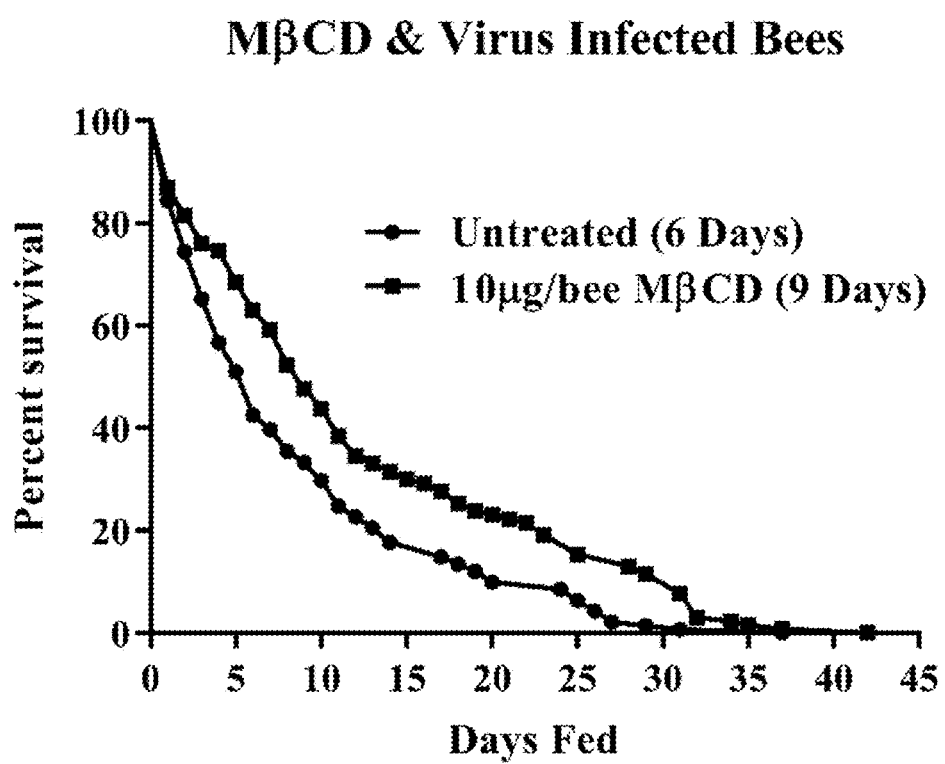
FIG. 7 shows dose response survival data for MBCD treatment related to virus-infected honey bees.
Figure 8A:
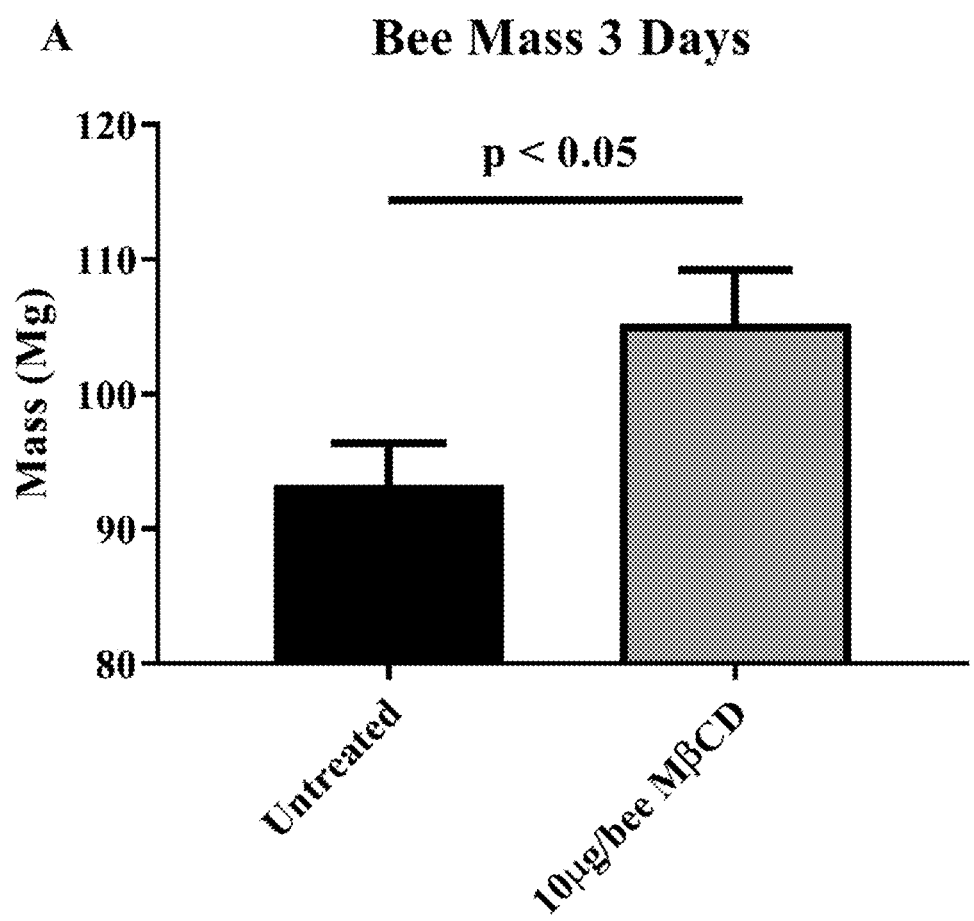
FIGS. 8A and 8B show dose response weight data for MBCD treatment related to virus-infected honey bees.
Figure 8B:
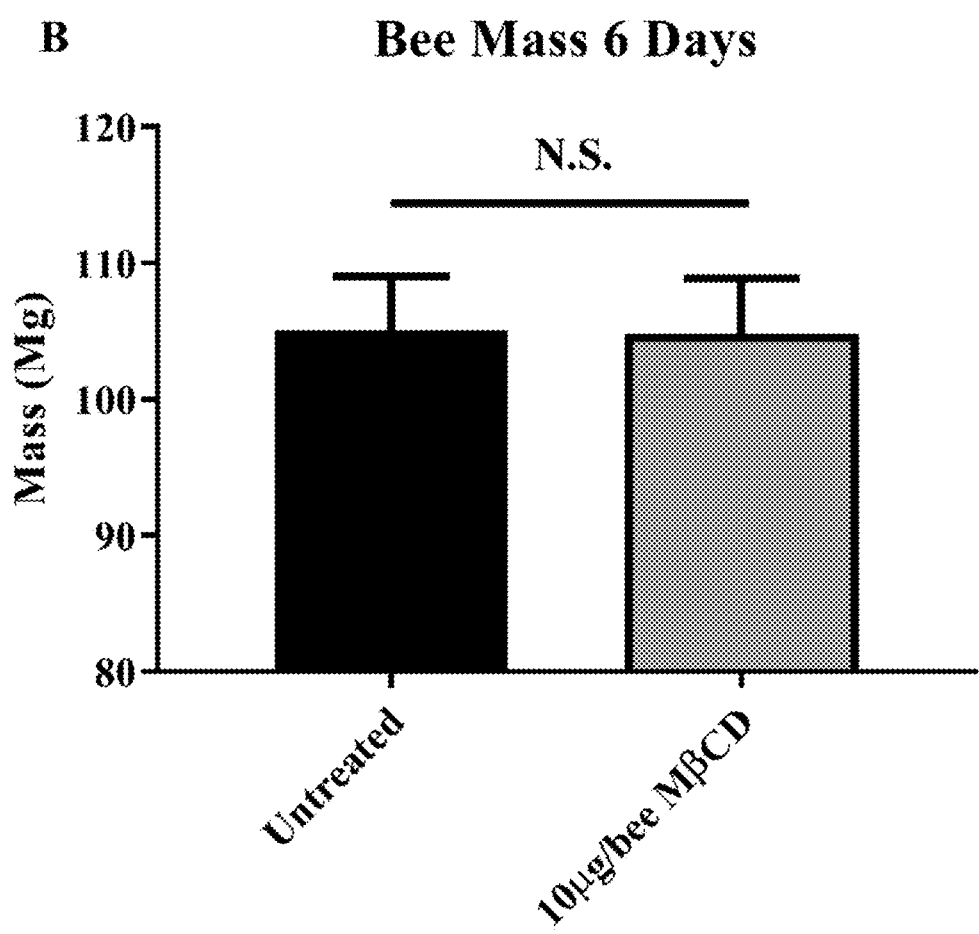

While both untreated and treated infected bees displayed short median lifespans (6 & 9 days respectively), bees treated with MBCD did surprisingly survive significantly longer. Untreated bees fed only 50% sucrose were compared to bees receiving 10 μg/bee MBCD in 50% sucrose (FIG. 7). Median survival was represented for each treatment by (# days). Curves were compared using Log-Rank Mantel-Cox ($p<0.001$) and Gehan-Breslow-Wilcoxon ($p<0.01$). Furthermore, treated bees were observed to have a significantly higher weight (n=24 bees per treatment) 3 days after feeding, which became statistically comparable 6 days after feeding. The mass (Mg) of control bees was compared to bees fed 10 μg/bee MBCD. Bees were measured 3 (FIG. 8A) and 6 (FIG. 8B) days post feeding. With average bee weight higher along with more bees present, the amount of work accomplished in the hive as a whole would be expected to increase. An unpaired, 2-tailed Student's T-Test was performed to determine statistical significance ($p<0.05$ at 3 days) and bars denote standard error.

Example 5

Figure 9A:
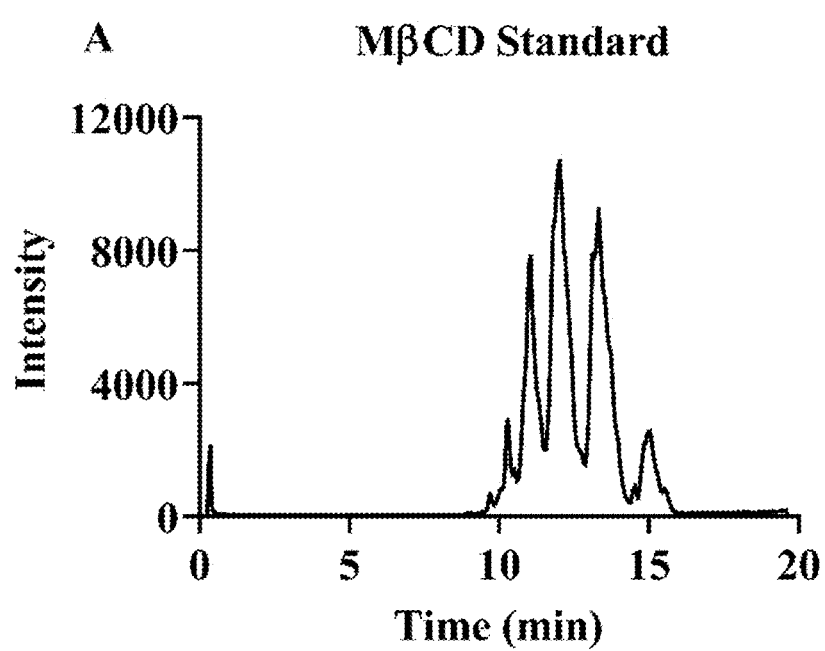
FIGS. 9A and 9B show mass spectrometry-based determinations of the presence of MBCD in treated honey bee colony honey stores.
Figure 9B:
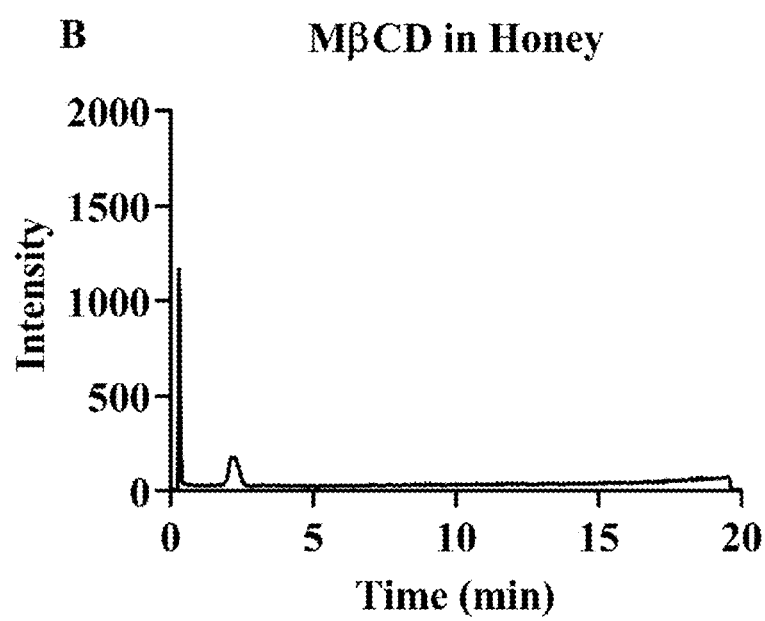

To verify any presence of residual CD in honey stores, the example illustrates mass spectrometry-based determination of the presence of MBCD in treated colony honey stores. FIG. 9A shows a baseline spectrum for the distinct peaks associated with MBCD. FIG. 9B shows a representative sample of honey extracted from colonies treated with 60 mg MBCD per month per colony, which surprisingly showed that residual MBCD was not present in the honey stores within the limits of detection and that the inventive treatment will not likely contribute to downstream contamination of honey.

Example 6

Figure 10A:
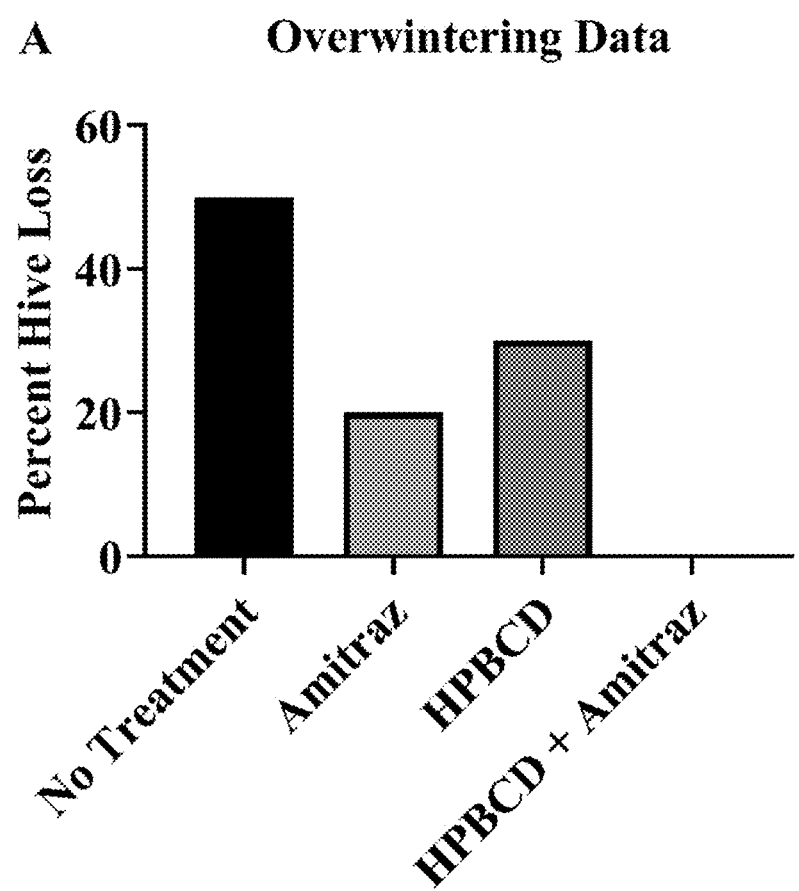
FIGS. 10A and 10B show hive loss results for overwintering hives treated with combinations of HBCD and acaricide.
Figure 10B:
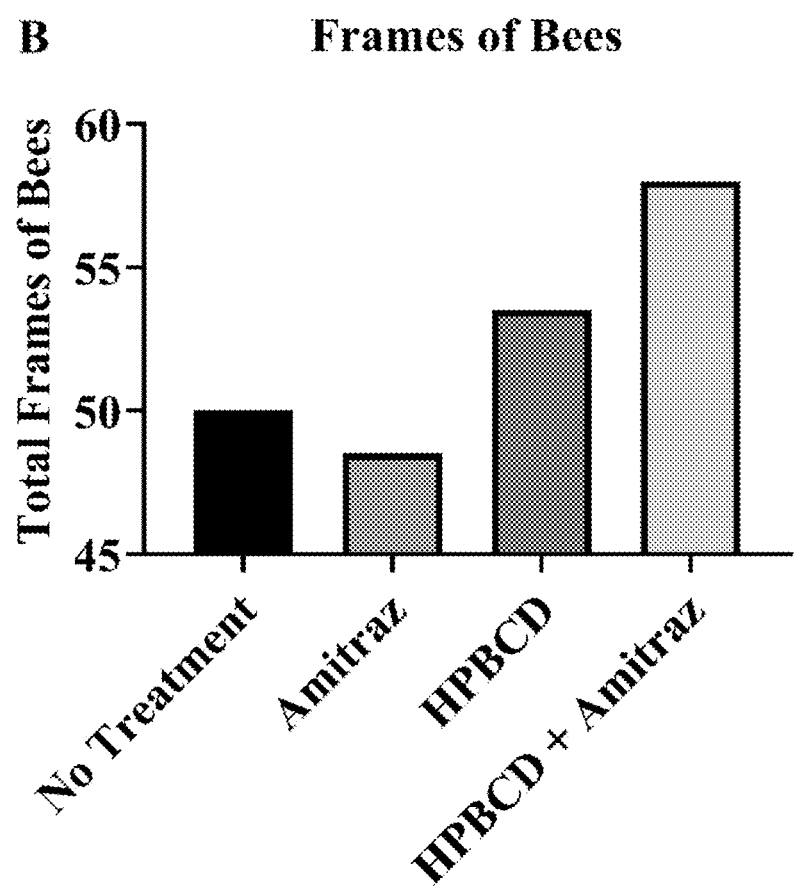

This example illustrates the use of HPBCD in a field setting. Four treatments with 10 colonies per treatment were performed as follows: (i) No HPBCD and no acaricide (No Treatment control), (ii) acaricide alone (Amitraz), (iii) HPBCD, and (iv) a combination of Amitraz and HPBCD. Colonies were fed treatments using a top box feeder in a "Langstroth Hive" from October to December, then surviving hives were counted in March of the following year and numbers of Langstroth frames containing bees were measured. About 50% of the colonies that received no treatment were lost; while it is a high level of loss it was within the expected range for hives that received no extra management besides sugar syrup supplementation (which agrees with the national average for untreated colonies). The group receiving only Amitraz, the current industry standard for mite control, lost about 20% of the colonies. HPBCD on its own was able to reduce hive loss to about 30%. Surprisingly and unexpectedly, when both Amitraz and HPBCD were combined, no colony losses were observed (FIG. 10A). With respect to bee populations within the hives it was observed that hives that did not receive HPBCD (no treatment 50 frames; Amitraz alone 48.5 frames) had fewer total frames containing bees compared to those receiving HPBCD (HPBCD alone 53.5 frames; HPBCD+Amitraz 58 frames) (FIG. 10B). Taken together these results demonstrate in the field that BCDs can increase the overwintering capability of honey bee hives, and surviving hives contain more bees for pollen and nectar collection in the spring. Perhaps of more importance, the use of Amitraz in conjunction with HPBCD had a demonstrable synergistic effect wherein no hives were lost and the greatest number of surviving bees was observed. Not intending to be bound by theory, one possible explanation for this profound effect is that Amitraz was lethal to mites based on contact (LC50), while the possible sub lethal and chronic affects for the honey bee were dosage based (LD50) as evidenced by slower behavioral response time (see e.g., De Mattos, 2017). It is likely the bees ingest the HPBCD and the Amitraz was sequestered rendering its effects on the bee diminished, while the groups that received no HPBCD were still susceptible to the effects of the acaricide.

Example 7

Figure 11:
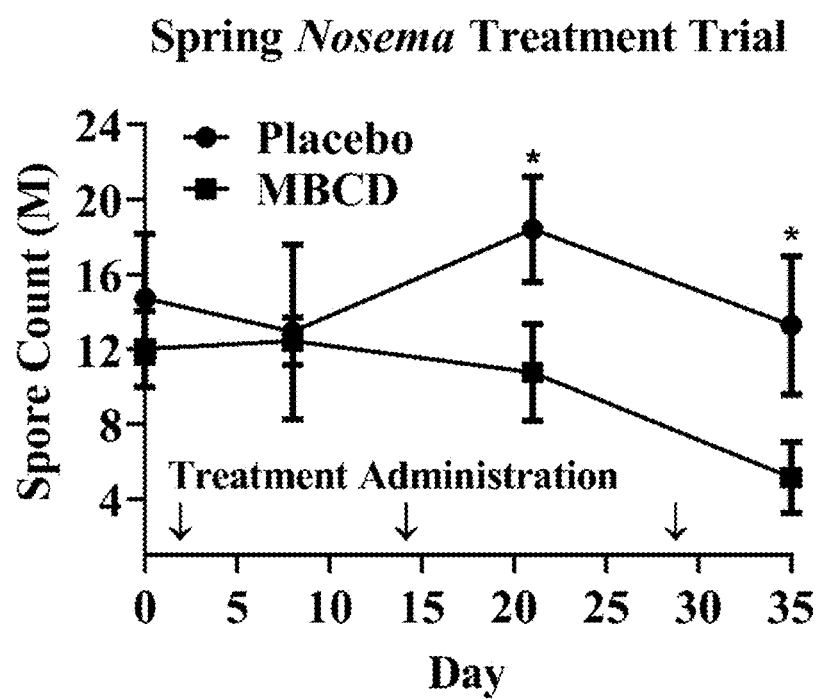
FIG. 11 shows that the administration of the MBCD formulation leads to a significantly reduced *Nosema* spore count in the midgut of bees.

This example illustrates the effectiveness of the inventive composition to reduce the number of *Nosema* spores in overwintering bees. The administered formulation contained 870 mg/L MBCD, 1.3 mg/L retinol, and 150 μg/L ergocalcitriol. The vitamins were added to counteract (i.e., induce differentiation of intestinal stem cells into epithelial cells) the greater loss of gut cells due to inducing autophagic cell death. The formulation was provided to bee colonies in sugar syrup at 500 mL volumes in a feeding apparatus (N=13 colonies for MBCD and 9 for placebo). Honey bee abdomens were homogenized, spore counts were measured via light microscopy, and spore counters were blinded from the treatments provided to colonies. Briefly, in the spring as bees convert from overwintering to pollen and nectar collecting spring bees, they tend to accumulate *Nosema* spores intracellularly in midgut epithelial cells which leads to digestive stress and poor colony health. Over-induction of autophagy leads to cell death, and the parasites along with the remnants of the cell are sloughed off into the midgut luminal space to be excreted. The results depicted in FIG. 11 show that the administration of the MBCD formulation leads to a significantly reduced spore count after 2 treatments per month. Not intending to be bound by theory, it was reported that MBCD increases basal autophagic flux to increase the number of midgut epithelial death and regenerative events for an accelerated return to equilibrium (see e.g., Dai et al., 2017).

While this invention may be embodied in many different forms, there are described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety, including any materials cited within such referenced materials. Furthermore, the invention encompasses any possible combination of some or all of the various embodiments and characteristics described herein and/or incorporated herein. In addition, the invention encompasses any possible combination that also specifically excludes any one or some of the various embodiments and characteristics described herein and/or incorporated herein.

The amounts, percentages and ranges disclosed herein are not meant to be limiting, and increments between the recited amounts, percentages and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 30%, preferably by as much as 20%, and more preferably by as much as 10% to a reference quantity, level, value, or amount.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims. Although any methods and materials similar or equivalent to those described herein can be used in the practice or testing of the present invention, the preferred methods and materials are herein described. Those skilled in the art may recognize other equivalents to the specific embodiments described herein which equivalents are intended to be encompassed by the claims attached hereto.

The claimed invention is:

1. A composition comprising: a mixture of at least one of methyl-β-cyclodextrin, hydroxypropyl-β-cyclodextrin, or a combination thereof, a carrier, and optionally one or more vitamins and/or nutrients; wherein the mixture provides an effective amount of the at least one cyclodextrin to a beehive to improve at least one health factor of bees in the beehive.

2. The composition of claim 1, wherein the carrier has a form selected from the group consisting of: an aqueous solution; a syrup; a solid; a spray; a gel; a dough; a granule; a powder; and combinations thereof.

3. The composition of claim 1, wherein the carrier comprises sucrose.

4. The composition of claim 1, wherein the effective amount of the at least one of methyl-β-cyclodextrin, hydroxypropyl-β-cyclodextrin, or a combination thereof is sufficient to mitigate exposure of the beehive to one or more pesticides.

5. The composition of claim 1, wherein the mixture comprises from about 0.04 g/L to about 4 g/L of the at least one of methyl-β-cyclodextrin, hydroxypropyl-β-cyclodextrin, or a combination thereof.

6. The composition of claim 1, wherein the effective amount of the at least one of methyl-β-cyclodextrin; hydroxypropyl-β-cyclodextrin; or combinations thereof is from about 1 µg to about 100 µg per bee in the beehive per month.

7. The composition of claim 1, wherein the effective amount of the at least one of methyl-β-cyclodextrin, hydroxypropyl-β-cyclodextrin, or a combination thereof is from about 1 µg to about 20 µg per bee in the beehive per month.

8. The composition of claim 1, wherein the one or more vitamins and/or nutrients is selected from the group consisting of: tocopherols, retinol, ergocalcitriol, and combinations thereof.

9. The composition of claim 8, wherein the mixture comprises from about 0.1 µg/L to a about 4 µg/L tocopherol.

10. The composition of claim 8, wherein the mixture comprises from about 0.13 mg/L to about 2.4 mg/L retinol.

11. The composition of claim 8, wherein the mixture comprises from about 1 µg/L to about 200 µg/L ergocalcitriol.

12. The composition of claim 1, wherein the mixture comprises an inclusion complex.

13. The composition of claim 12, wherein the inclusion complex comprises at least one fat-soluble component.

14. The composition of claim 13, wherein the at least one fat-soluble component comprises at least one tocopherol.

15. The composition of claim 14, wherein the at least one tocopherol is selected from the group consisting of highly active isomers of the tocopherol-tocotrienol family.

16. The composition of claim 1, wherein the at least one health factor of the bees in the beehive are selected from the group consisting of: increased average lifespan of individual bees; enhanced overall bee health; improved overwintering capacity of the beehive; reduced pesticide toxicity impact on the bees; reduced viral load measured in bees in the beehive; reduced fungal spores in the bees; and combinations thereof.

17. A method of improving beehive health, the method comprising administering the composition of claim 1 to the beehive.

18. The method of claim 17, wherein the mixture provides the effective amount of the at least one of methyl-β-cyclodextrin, hydroxypropyl-β-cyclodextrin, or a combination thereof to the beehive to improve the lifespan of bees in the beehive in a statistically significant fashion as compared to a nontreatment lifespan providing no cyclodextrin to the beehive.

19. The method of claim 17, wherein the mixture provides the effective amount of the at least one of methyl-β-cyclodextrin, hydroxypropyl-β-cyclodextrin, or a combination thereof to the beehive to improve the lifespan of bees in the beehive and to reduce spread of an infectious disease in the beehive.

20. The method of claim 17, further comprising a feeding apparatus with the composition of claim 1 disposed therein, wherein the feeding apparatus is associated with the beehive to allow bees access to the mixture.

21. An apparatus comprising: a feeder including the composition of claim 1, wherein the feeder allows bees in the beehive to access the mixture.

22. The apparatus of claim 21, wherein the feeder reduces access to antagonistic pests.

23. The apparatus of claim 21, wherein the feeder is selected from the group consisting of: a community feeder; a Boardman entrance feeder; a gravity fed waterer; a double hive top feeder; a quad hive top feeder; a round top feeder; a pollen syrup top feeder; a division board feeder; a bucket feeder; and combinations thereof.

* * * * *